United States Patent
Heiniger et al.

(10) Patent No.: US 7,182,749 B2
(45) Date of Patent: Feb. 27, 2007

(54) INJECTION DEVICE AND NEEDLE COVERING DEVICE

(75) Inventors: Hanspeter Heiniger, Lotzwil (CH); Simone Geiser, Langnau (CH)

(73) Assignee: TecPharma Licensing AG, Burgdorf (CH)

( * ) Notice: Subject to any disclaimer, the term of this patent is extended or adjusted under 35 U.S.C. 154(b) by 576 days.

(21) Appl. No.: 10/225,571

(22) Filed: Aug. 21, 2002

(65) Prior Publication Data

US 2003/0040716 A1 Feb. 27, 2003

(30) Foreign Application Priority Data

Aug. 22, 2001 (DE) .................. 101 41 039

(51) Int. Cl.
*A61M 37/00* (2006.01)
(52) U.S. Cl. ............... 604/131; 604/135; 604/207; 604/198; 128/1
(58) Field of Classification Search ........... 604/187, 604/197, 117, 192, 156, 204, 131, 134, 135, 604/263, 232, 233, 234, 198, 93.01, 236
See application file for complete search history.

(56) References Cited

U.S. PATENT DOCUMENTS

| | | | | |
|---|---|---|---|---|
| 2,565,081 A | * | 8/1951 | Maynes ................. 604/136 |
| 4,804,372 A | * | 2/1989 | Laico et al. ............ 604/198 |
| 4,915,701 A | * | 4/1990 | Halkyard ............... 604/198 |
| 5,104,386 A | * | 4/1992 | Alzain .................. 604/232 |
| 5,611,784 A | * | 3/1997 | Barresi et al. ......... 604/211 |
| 5,681,291 A | * | 10/1997 | Galli ................... 604/192 |
| 5,823,998 A | * | 10/1998 | Yamagata .............. 604/131 |
| 6,090,070 A | * | 7/2000 | Hager et al. .......... 604/131 |
| 6,238,371 B1 | | 5/2001 | Himbert et al. | |
| 6,416,497 B1 | * | 7/2002 | Kirk .................... 604/198 |

FOREIGN PATENT DOCUMENTS

DE 4013769 10/1991

* cited by examiner

*Primary Examiner*—Nicholas D. Lucchesi
*Assistant Examiner*—Aamer S. Ahmed
(74) *Attorney, Agent, or Firm*—Dorsey & Whitney LLP

(57) ABSTRACT

The present invention is an injection device for injecting a fluid product from a reservoir includes a casing having at least two casing portions. The device also includes a mounting for the reservoir such as an ampoule containing the fluid product to be administered, wherein one casing portion at least partially surrounds the reservoir. An activating element for triggering fluid product administering is provided. The at least one casing portion surrounding the reservoir is movable relative to the other casing portion or parts, such that by moving the movable casing portion, the reservoir and/or an injection needle connected to the same is accessible from the outer side of the casing, in order to be replaced.

25 Claims, 11 Drawing Sheets

INJECTION DEVICE AND NEEDLE COVERING DEVICE

CROSS-REFERENCE TO RELATED APPLICATION(S)

The application claims the priority of German patent application No. DE 101 41 039, filed on Aug. 22, 2001.

BACKGROUND OF THE INVENTION

1. Field of the Invention

The present invention relates to an injection device for injecting a fluid product that includes a needle covering device.

2. Description of the Related Art

Injection devices are used for administering a fluid product such as a medicine, an infusion solution, or a contrast agent from a reservoir, e.g., an ampoule. An injection needle or cannula is used to inject the fluid product into human or animal tissue. When the fluid product in the reservoir is depleted, the reservoir should be able to be quickly and easily replaced.

For safety reasons and to prevent the fluid product from being unintentionally administered, the injection needle may be covered when not in use. However, the injection needle should be quickly and reliably accessible when the fluid product is to be administered. Moreover, since many users of injection devices have a psychological aversion (so-called "needle phobia") to injection needles, it may be beneficial to obscure from view at least a portion of the injection needle.

Slip-on covering caps which can be removed or pushed together for covering needles are disclosed in WO 96/11026. Alternatively, retractable needle covering devices cover at least the end of the injection needle. The cover is retracted so that the injection needle can be injected into the tissue.

Such needle covering devices are disclosed in U.S. Pat. No. 4,804,372 and DE 40 13 769 A1. These injection devices are comparatively long. Thus, when attempting to place the injection needle at an angle to the surface of the tissue, the injection needle may bend and the needle and cover may draw relatively near, to the point where the injection needle jams in the needle cover. Moreover, replacing the fluid product reservoir is complicated, since the needle covering device has to be removed before the reservoir is replaced. The covering device must then be replaced afterwards on the new reservoir, which in the case of complicated injection devices, for example those comprising electronics, can lead to significant time loss and sources of danger.

SUMMARY OF THE INVENTION

In one embodiment, the present invention is an injection device wherein a fluid product reservoir, e.g., an ampoule, can be replaced quickly and easily. Moreover, the injection device is reliable and easy to handle. A needle covering device for such an injection device is also to be provided.

In one embodiment, the injection device includes a casing having at least two casing portions; a mounting for the reservoir and an activating element for triggering fluid product administering. One casing portion at least partially surrounds the reservoir and can be moved relative to the reservoir (or to the other casing portions). Thus, by moving the movable casing portion, the reservoir and/or an injection needle connected to the reservoir is accessible from the outer side of the casing and can be replaced.

Thus, the reservoir, e.g., an ampoule, can be changed without having to open the actual casing of the injection device. In this respect, the movable casing portion may be formed comparatively small in comparison to the non-movable casing portions; that is, adapted to the size of the reservoir to be replaced. Thus, the actual casing or main casing of the injection device can contain the elements necessary for it to operate. For example, complex mechanism such as a counter and display means (including any required circuitry) can be disposed within the casing. Additionally, such parts can include a dosing means, an activating means and similar elements that are not altered in their positions relative to each other when a reservoir is replaced. Thus, their settings relative to each other also do not have to be reset when the reservoir is replaced. Moreover, dirt and moisture are prevented or at least hindered in reaching sensitive parts. Thus, the injection device can be operated more reliably and with less maintenance. Furthermore, the more sensitive parts of the injection device can be sealed against dirt, dust and moisture and other environmental influences.

In one embodiment, the movable casing portion can be moved in an axial direction (relative to the reservoir) between a forward position and a retracted position. Replacement of the reservoir and/or an injection needle occurs when the moveable casing is in the retracted position and prevented (or at least hindered) in the forward position. The movable casing portion may also be movable in other directions relative to the reservoir. For example, the moveable portion may move perpendicular to the axial direction, i.e., away from the main casing of the injection device, in order to provide a suitable space such that the reservoir and/or the injection needle can be grasped from the outer side of the casing for replacement.

In one embodiment an injection device includes a casing having at least two casing portions, a mounting for the reservoir and an activating element for triggering fluid product administering. One casing portion at least partially surrounds the reservoir and can be moved relative to the reservoir or to the other casing portions of the injection device, such that by moving the movable casing portion, the reservoir and/or an injection needle connected to the same is accessible from the outer side of the casing, in order to be replaced.

For injection into tissue, the needle protrudes beyond a forward end of the injection device. The position of the movable casing portion is adapted to the position and length of the injection needle. Thus, when the casing is in a forward protective position, the forward end of the movable casing portion protrudes beyond the forward end of the casing of the injection device and the needle. However, in order to enable the fluid product reservoir to be easily replaced, the movable casing portion can be moved back beyond the forward end of the reservoir, where the injection needle is conventionally connected to the reservoir, such that the forward part of the reservoir can be handled. The needle covering device can be retracted back beyond the forward end of the reservoir by a distance that approximates the width of an average finger, so that the reservoir can at least be grasped by two fingers for removal.

The casing portion can include a forward part and a forward end of the reservoir can protrude from the forward end of the forward part and the movable casing portion can be movable back at least as far as the forward end of the forward part, such that the forward end of the reservoir can easily be grasped from the outer side of the casing, i.e., from its facing side, in order to be replaced.

In one embodiment, the movable casing portion is simultaneously formed as a needle cover for the injection needle and serves to protect against the injection needle being unintentionally injected into a tissue or unintentionally touched.

In one embodiment, the needle cover includes at least one section which can be moved relative to the casing, or is formed by such a section, such that at least a forward end of the injection needle is covered by the cover in a forward protective position of the cover, and protrudes from a forward end of the cover in a retracted position of the cover. Thus, by placing the injection device together with the needle cover on the tissue and by pressing the injection device as a whole, the injection needle can be injected into the tissue without the user seeing the injection needle before it injects.

In one embodiment, the cover is substantially tube-shaped and has a circular, elliptical, rectangular or polyhedral cross-section. Due to a lateral opening in the cover, it can be laterally attached to the injection device, at least partially surrounding the fluid product reservoir. This type of arrangement enables a range of advantages. For example, the fluid product reservoir can be attached laterally to the injection device, such that the conventionally used elongated reservoirs (e.g., ampoules) can be practically supported along their entire length on a side wall of the casing. Thus, the reservoir attachment is mechanically stable, especially with regard to twisting and bending forces. Due to the lateral arrangement of the reservoir, injection devices of shorter lengths can be provided, given fluid product reservoirs of comparable length, such that overall weaker leverage forces are acting on the injection needle and/or the needle covering device. The somewhat larger width of such an injection device is not disruptive. Rather a large width is often advantageous, since otherwise relatively narrow, pen-shaped injection devices can then be formed such that they are easily grasped, for example fitting into a patient's fist.

When the fluid reservoir is laterally attached to an injection device, the reservoir together with the injection needle is more accessible and can be more easily replaced and monitored. For example, the fluid product reservoir can easily be grasped for replacement, once the cover has been retracted. For example, the reservoir can be grasped and rotated and thus screwed in or out. The injection needle is nonetheless reliably and mechanically covered in the forward protective position of the needle cover, since when attached laterally to a casing of an injection device, the needle cover is laterally supported substantially along its entire length.

In embodiments using, e.g., syringes or ampoules having a circular cross-section, the cover has a semi-circular cross section with two side wall sections running substantially in a straight line, as seen in cross-section. The side wall sections laterally define an opening in the cover. The diameter of the semi-circular section is adapted to the diameter of the fluid product reservoir. The semi-circular section enables a structurally stable and visually appealing cover. The length of the side wall sections is selected such that, when the needle covering device is arranged laterally on an injection device, the side walls of the fluid product reservoir are supported by a side wall of the injection device. In this way, the fluid product reservoir is held in a structurally stable way. The opening angle of the opening can also be selected such that the cover encompasses the fluid product reservoir by more than 270°, so that a syringe or ampoule can be supported in a cavity arranged in a side wall of the injection device.

In one embodiment, the moveable portion of the cover is preferably returned to the forward protective position by a restoring element, such that the injection needle is always covered in its resting state. At least one protrusion can be provided on the cover to hold the restoring element. The protrusion meshes with a longitudinal slit of the injection device and is guided in it when retracted. The protrusion includes a trunnion or a comparable mounting for the restoring element. The other end of the restoring element is supported in the casing of the injection device. Thus, when the cover is retracted, the restoring element is compressed and the compression force of the spring thus increased. This feature enables the injection device to be formed in a particularly space-saving way.

Alternatively, in one embodiment, the cover can be formed as one piece, wherein the cover interconnects with at least one guide in the casing of the injection device and can be moved, that is guided, relative to the casing.

In one embodiment, the cover is designed in at least two pieces, and includes one or more covering elements that can be longitudinally telescoped relative to one or more fixed portions. The cover can be formed from two pieces, having a rear and a forward element, each having at least one mutually corresponding guide element, which co-operate to enable the forward element to be guided when it is retracted. Guide elements in the form of grooves and corresponding protrusions work well. In particular those having a rectangular, circular or elliptical profile work well, since these enable the elements to be easily joined together and arranged in a mechanically stable way.

The rear covering element includes at least one attaching element which serves to fixedly attach the rear element to an injection device. Locking elements which can be non-detachably or detachably locked into recesses or protrusions on an injection device may be used. This allows the needle covering device to be pre-assembled and then attached to an injection device as a module. Alternatively, a needle covering device which is variable in length within itself could also be formed as expansion bellows.

In one embodiment, the rear and forward portions of a two-piece cover can each include at least one extended section having a mounting or receptacle for holding a restoring element. The restoring element, in particular a spring, can be supported in a positionally and dimensionally stable way in the extended section.

In one embodiment, the needle covering device includes at least one latching means, to prevent the cover from retracting (or advancing in some cases from either extreme position or any intermediate position, if the latching means is in its latching position. In this way, the cover can effectively be prevented from being inadvertently retracted. Latching has also proven to be advantageous in the retracted position of the cover, since the cover then no longer has to be held back manually to replace the fluid product reservoir. Rather the user has both hands free to handle the reservoir.

In one embodiment, the mounting for the restoring element is arranged outside the center of the needle covering device, when seen in cross-section. In this way, a restoring force which acts substantially at the center of the injection device can be realized, even when the needle covering device is arranged laterally on the injection device. The injection device therefore needs merely to be placed substantially perpendicular on the tissue and pressed down against the restoring force of the restoring element. Since the restoring force acts substantially in the center, the danger of the injection needle or the injection device tipping or bending is effectively reduced.

The cover may be formed at least partially from a transparent material, such that the level of the fluid product reservoir and/or the state of the injection needle can be viewed. In one embodiment, the forward end of the cover is opaque, such that at least the forward end of the injection needle is not visible, which otherwise could intimidate the user.

The needle covering device can be laterally attached to a casing of an injection device.

When the cover of the injection needle includes two or more pieces, receptacles for accommodating attaching elements may be provided in a forward part of the casing of the injection device, in order to securely attach the non-moving section of the cover to the casing of the injection device. At least one longitudinal slit can also be provided in the upper part, to guide a protrusion provided on the longitudinally movable section of the cover.

The needle covering device may also be used to limit the penetration depth of the injection needle into the tissue. To this end, a stopper can be provided on the injection device or in the needle covering device, for setting the penetration depth. This stopper can be adjustable. In this way, an injection device with even fewer components can be provided.

In one embodiment, a needle covering device includes a cover which may be connected to the casing of the injection device and has at least one section which may be moved relative to the casing of the injection device, such that at least the forward end of the injection needle is covered by it in a forward protective position, and such that the forward end of the injection needle protrudes from a forward end of the cover in a retracted position of the cover, such that the non-covered art of the injection needle can be injected into the tissue. Furthermore, the needle covering device includes at least one guide element for guiding the cover or at least the movable section of the cover when it is moved between the forward protective position and the retracted position. A side wall of the cover includes an opening at least at its forward end, said opening enabling the fluid product reservoir and/or the injection needle to be replaced, in the retracted position of the cover, and at least hinders or as far as possible prevents them from being replaced, in the forward protective position of the cover.

DETAILED DESCRIPTION

Figure 1:
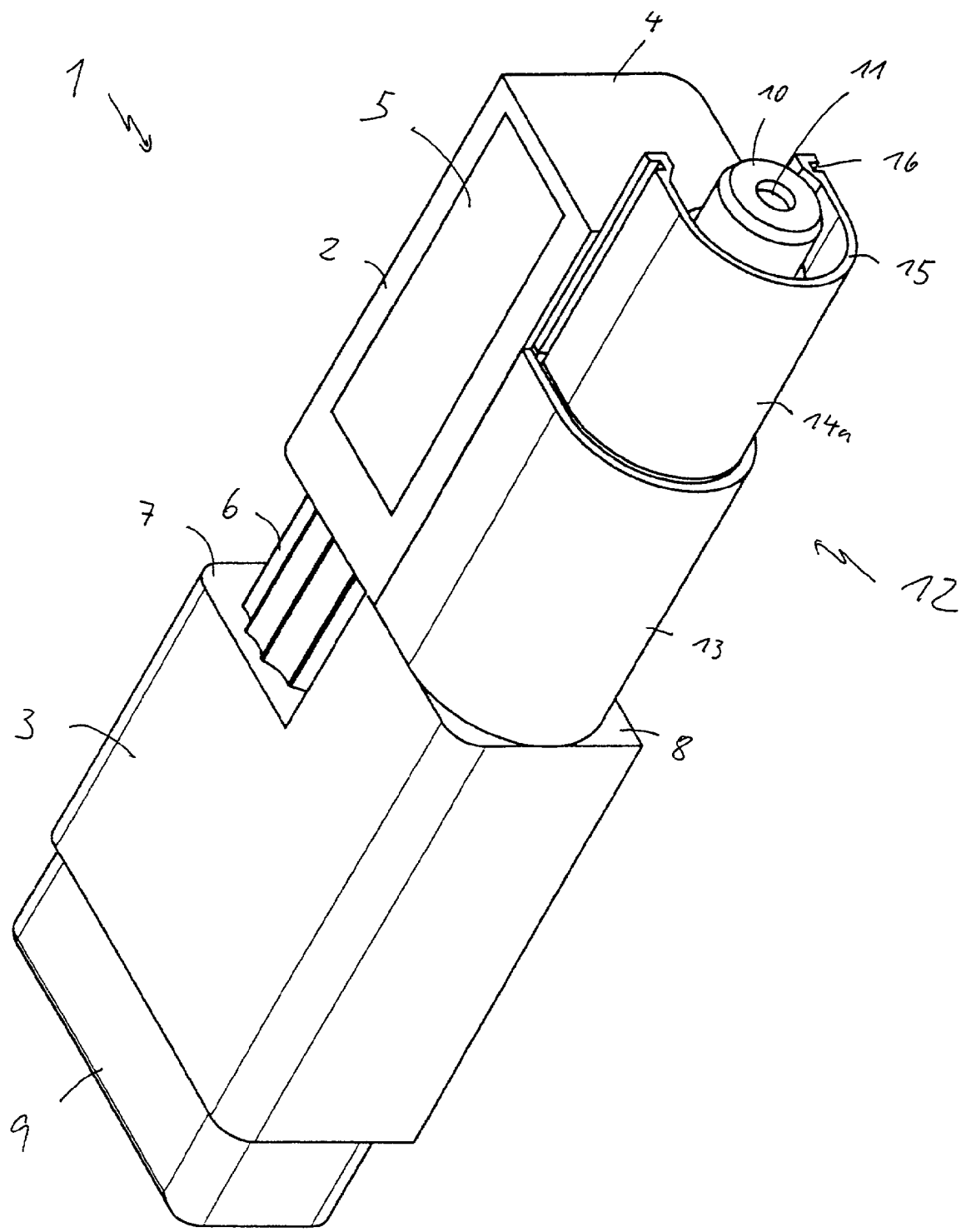
FIG. 1 is a perspective view of an injection device with a needle cover in a retracted position.

In the figures, identical reference numerals indicate the same or similar elements.

FIG. 1 is a perspective view of an injection device 1. The injection device 1 has a needle cover 12 illustrated in a retracted position. The injection device 1 includes a casing including a forward part 2, a rear part 3, and a needle cover 12 connected to the forward part 2. The injection device 1 also has a dosing wheel 6 for setting the fluid product dosage and an activating button 9 for injecting the fluid product. An electronic system can be provided in the forward part 2, for controlling all the processes of the injection device. An ampoule 10 is laterally supported on the forward part 2.

Figure 3:
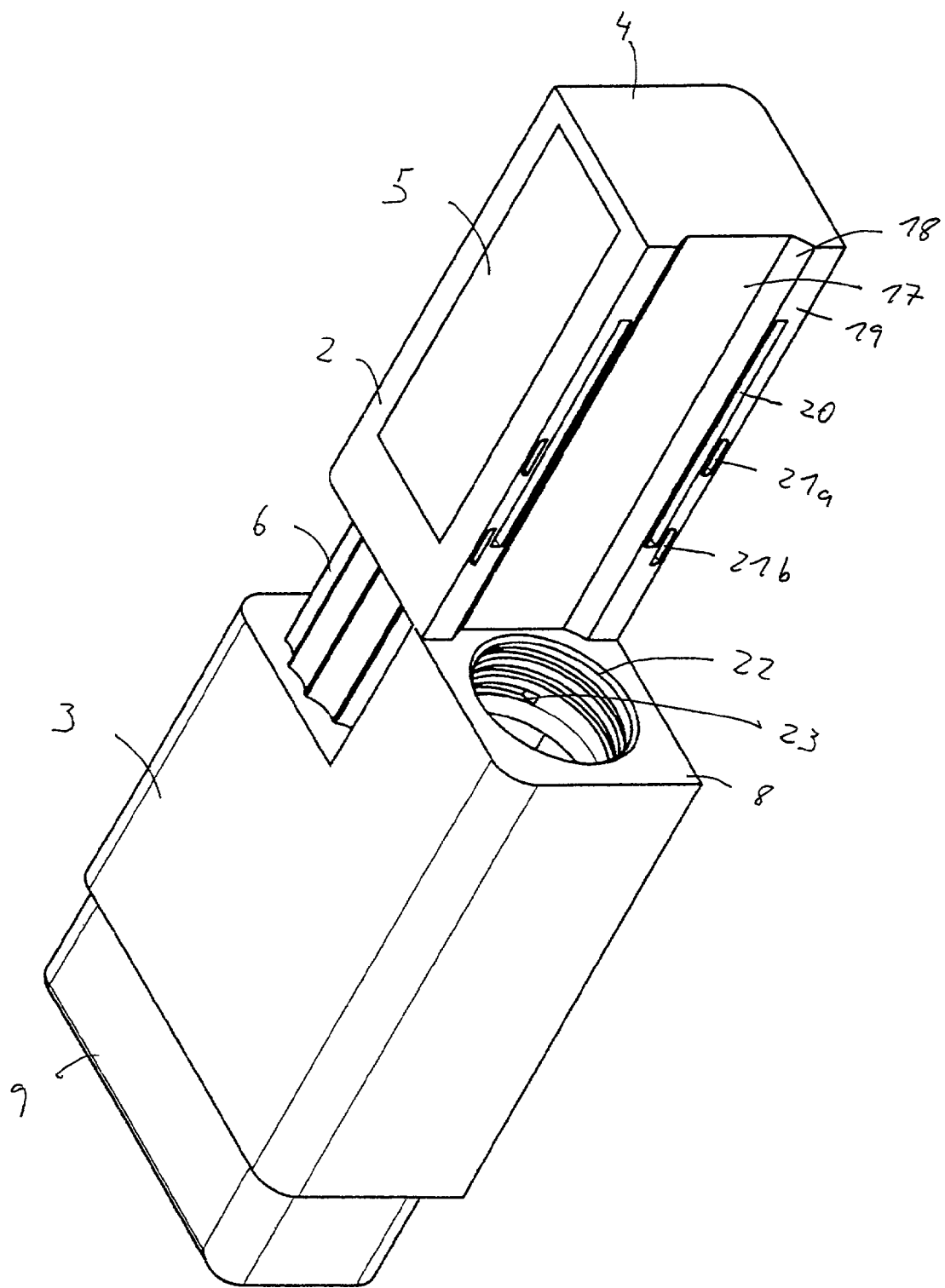
FIG. 3 is a perspective view of the injection device of FIG. 1, without the needle cover.

As illustrated in FIG. 3, a recess formed by chamfers 18 and an inner side 17 can be provided in the forward part 2, the recess preferably being adapted to the shape of the ampoule 10. A rear end of the ampoule 10 is screwed into the thread 22. The recess 23, which a latching element can latch into, serves to position the ampoule.

Other operational elements can be accommodated in the forward part 2, in particular a dosing means and a counter and display means, may be provided, for example, in the opening 5 of the forward part 2 or on the rear part 3. In order to sufficiently protect these elements from the environment, in particular from dirt and moisture, the forward part 2 (or any portion of non-moving casing portions) can be sealed against the environment. Since the reservoir or ampoule 10 is laterally attached to the casing of the injection device and the forward element 14 of the needle cover 12 can be moved, the reservoir or ampoule 10 can be replaced without the forward part 2 or the other non-movable casing portions having to be opened.

As illustrated in FIG. 1, the needle cover 12 is laterally attached to the forward part 2. The needle cover 12 is designed in two pieces and includes a positionally stable (i.e., non-moving when attached to the injection device) rear element 13 connected to the forward part 2. Cover 12 also includes a forward element 14 that is longitudinally movable relative to the rear element 13, of which only the forward section 14a is visible in FIG. 1. Alternatively, the needle cover 12 can also be formed as one or a number of pieces. Where the needle cover 12 is formed as one piece, it is appropriately guided and held in guide elements of the forward part 2 of the casing.

Figure 2:
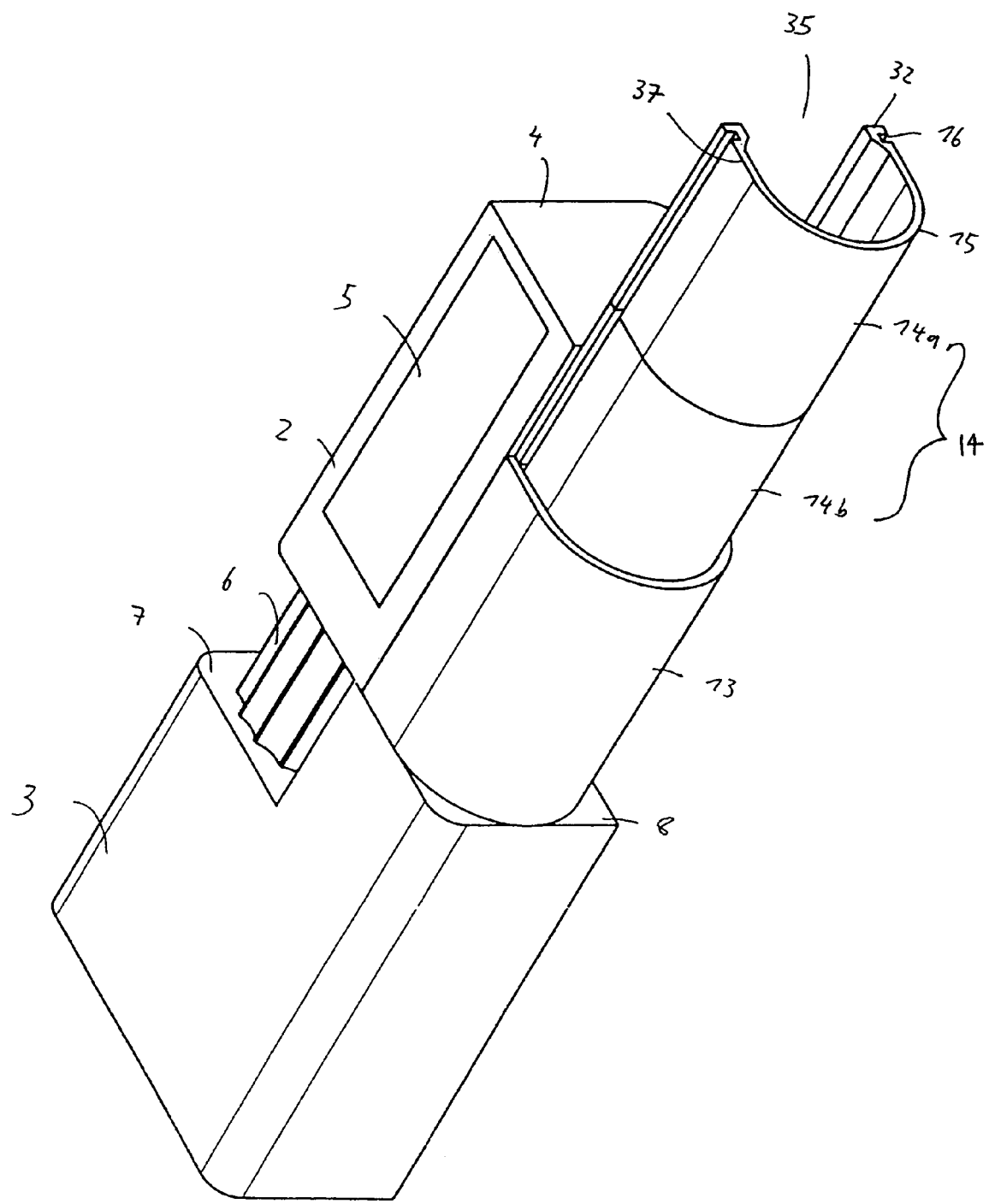
FIG. 2 is a perspective view of the injection device of FIG. 1, with the needle cover in the forward protective position.

With reference to FIGS. 1 and 2, the forward element 14 can be longitudinally telescoped relative to the rear element 13 though it does not matter which of the two elements surrounds the other in the retracted position. To inject the fluid product, the forward element 14 is retracted into the rear element 13 against the restoring force of a restoring element (described below) until an appropriate penetration depth is reached. This depth can be predetermined (or maximized) by the forward end of the ampoule 10, where the injection needle (not shown) is inserted into the opening 11. Alternatively, a stopper (not shown) is provided either in the casing of the injection device or in the needle cover 12, to adjustably predetermine the maximum retracted position of the forward element 14.

As shown in FIG. 1, the forward end of the ampoule 10 protrudes beyond the forward end 4 of the forward part 2, such that the ampoule 10 is easily accessible for removal.

The forward end of the ampoule 10 can instead end flush with the forward end 4 or the forward end 4 can protrude beyond the forward end of the ampoule 10. If the forward edge 15 of the forward element 14 can be retracted back beyond the forward end of the ampoule 10 (towards the rear element 13), for example, by at least the width of a finger, such that the forward section of the ampoule 10 is easily accessible for handling, the replacement of ampoule 10 becomes easier.

As illustrated in FIG. 2, a guiding groove 16 is formed in each of the two side walls 37 for guiding the forward element 14. The guiding groove 16 runs substantially in a straight line, and the grooves extend as far as the forward end of the forward element 14, but can also be limited by a collar at the rear end of the forward element 14, in order to limit the forward extreme position of the forward element 14. In this way, the forward element 14 and rear element 13 can be joined together before the needle cover 12 is attached to the forward part 2.

Figure 4:
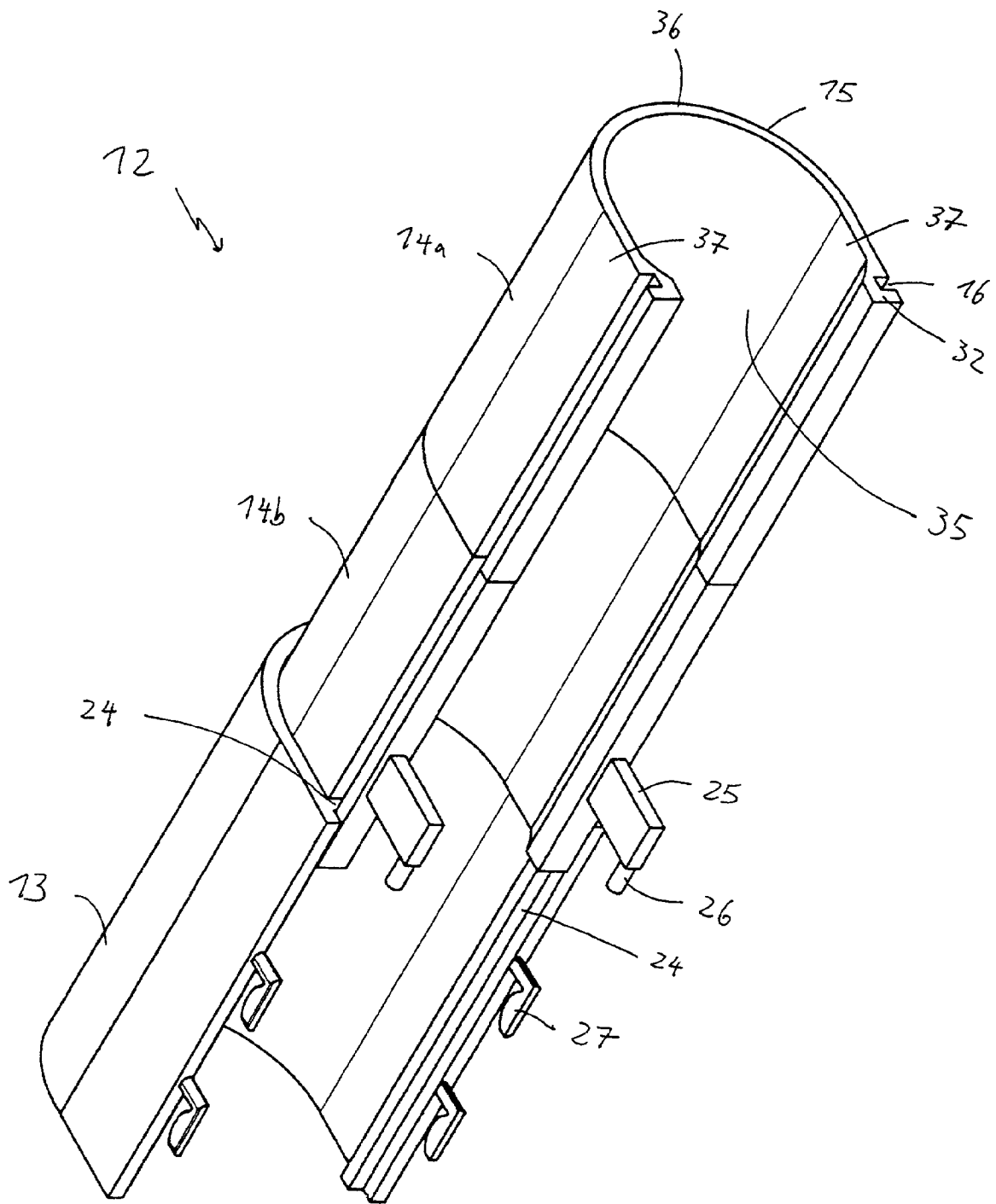
FIG. 4 is a needle cover.

As illustrated in FIG. 4, the guiding protrusion 24 meshes with the guiding groove 16 and has a profile that is adapted to the profile of the guiding groove 16. In order to form the guiding groove 16, extended sections 32 are formed on the longitudinal sides of the side walls 37, the guiding groove 16 being recessed in said sections.

FIG. 4 also shows a perspective view of the needle cover 12 from the inside. Alongside the section 14a (which may be opaque to limit viewing of the needle), the forward element 14 includes a section 14b which may be transparent so that the level of the ampoule and also the state of the injection needle can easily be appraised from the outside.

A protrusion 25 is provided on the longitudinal side of a side wall 37. The protrusion interconnects with the longitudinal slit 20 shown in FIG. 3 and is guided in the slit 20 when the forward element 14 is retracted. The forward extreme position of the forward element 14 can be defined by the upper area of the protrusion 25. To join the needle cover 12 together, the guiding protrusion 24 is inserted into the guiding groove 16. The forward extreme position of the forward element 14 can be limited at the rear end of the guiding groove 16 by a heel (not shown).

As shown in FIG. 4, the elongated side walls 37 limit the opening 35 provided in the needle cover 12. The opening 35 extends substantially along the entire length of at least the longitudinally movable section of the needle cover 12, i.e., substantially along the entire length of at least the forward element 14. The non-moving rear element 13 attached to the injection device 1 likewise includes a lateral opening 35. In alternative embodiments, however, the non-moving element 13 can also be formed by the casing or a part of the casing of the injection device, in which case no lateral opening 35 needs to be provided. The width of the opening 35 is selected to ensure that the ampoule provided inside the needle cover 12 is appropriately supported and covered and that the injection needle and/or the ampoule is sufficiently easy to handle when the needle cover 12 is retracted. The lateral opening 35 extends substantially along the entire width of the needle cover 12, such that the opening angle of the opening 35 is substantially 90°.

In the pre-assembled state, the needle cover 12 is placed on the inner side 17 of the forward part 2 such that the protrusions 25 interconnect with the longitudinal slit 20 and the attaching elements 27 interconnect with the recesses 21a, 21b provided in the lateral edge of the inner side 17. The attaching elements 27 are preferably locking elements which lock into the recesses 21. Other appropriate detachable or non-detachable attaching techniques may be utilized. The forward part 2 of the casing and the shell-shaped needle covering device forms a closed or substantially closed hollow cylindrical space. That is, the forward part 2 of the casing closes the opening 35 in the needle covering device.

Figure 5:
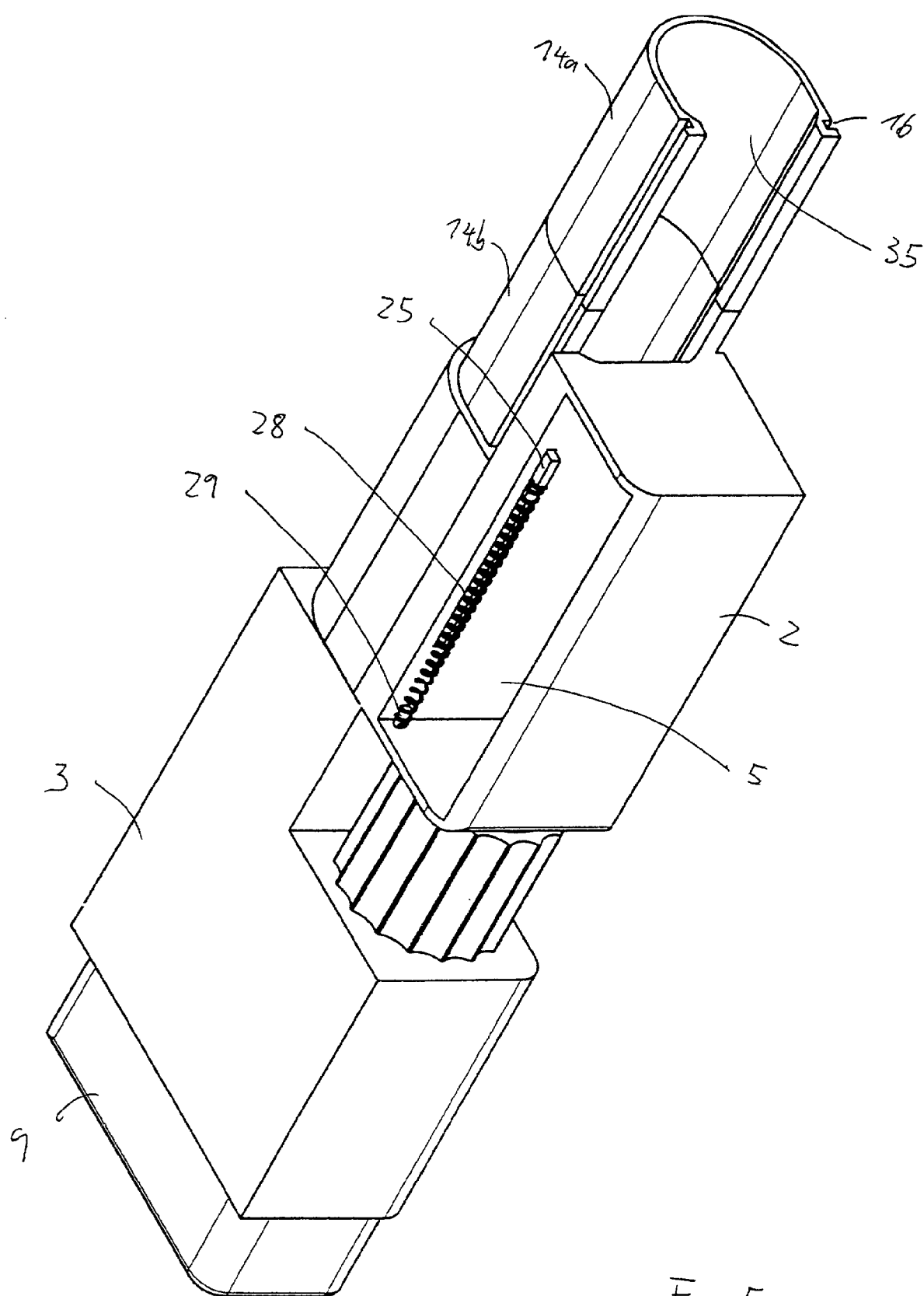
FIG. 5 is a perspective view of the injection device in accordance with the first embodiment, in which the arrangement of the restoring element is shown.
Figure 6:
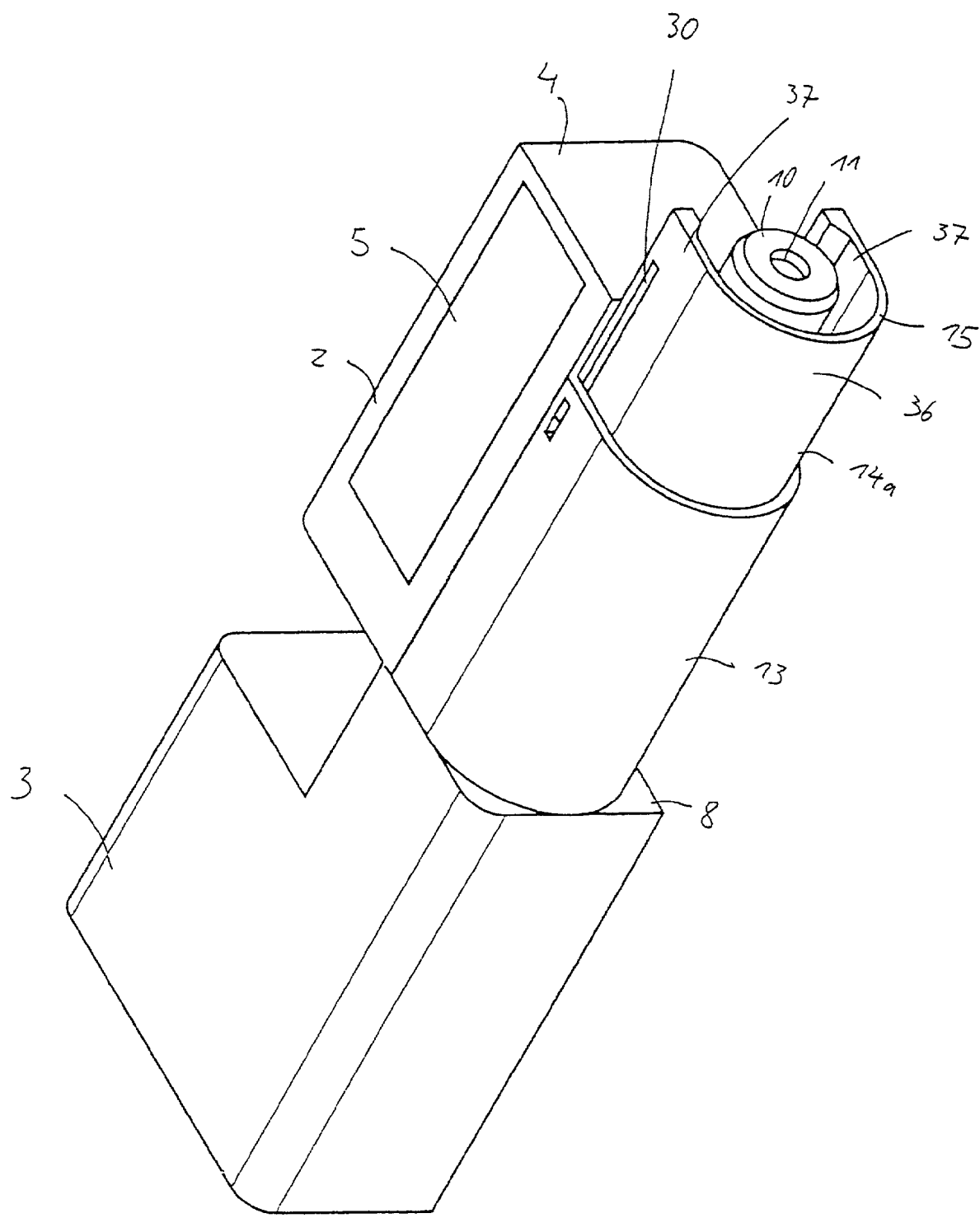
FIG. 6 is a perspective view of an injection device with a needle cover in a retracted position.
Figure 7:
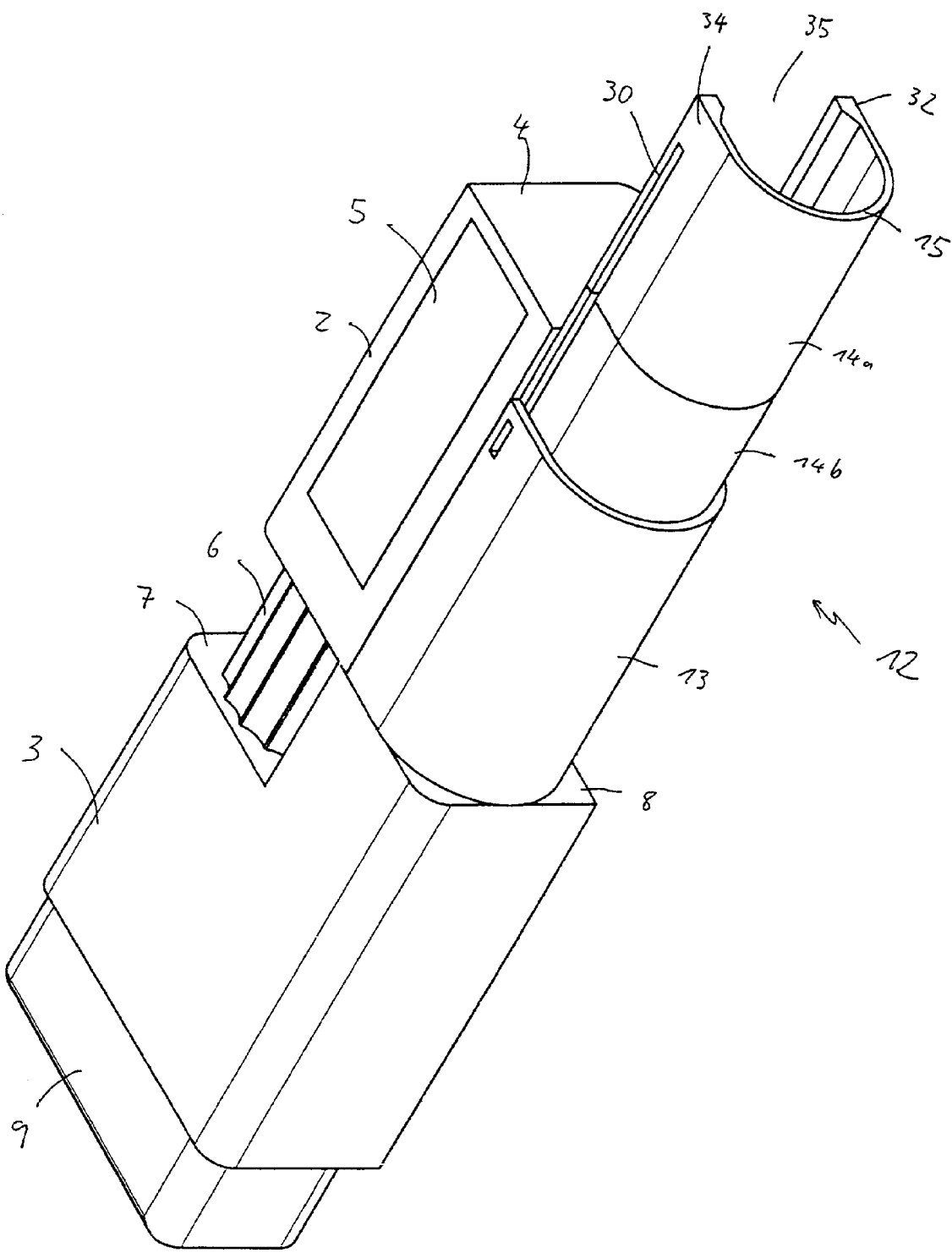
FIG. 7 illustrates the injection device of FIG. 6, with the needle cover in the forward protective position.

As shown in FIG. 4, each protrusion 25 comprises a trunnion 26 on which a spring 28 is placed. The spring 28, shown in FIG. 5, serves as the restoring element for restoring the forward element 14. The other end of the spring 28 is placed on the trunnion 29 arranged on the base of the forward part 2. In order to assemble the needle cover 12, the springs 28 are slipped onto the trunnions 29. The springs are appropriately pressed together, and the needle cover 12 is placed on the inner side 17 of the forward part 2. The protrusions 25 protrude into the longitudinal slit 20. The spring 28 is then relaxed and is slipped onto the trunnion 26. For laterally guiding the spring 28, a longitudinal guide, e.g., a slip on sleeve, can be provided in the inner side of the forward part 2.

An electronic control system can be provided to control the injection device 1, and can be inserted into the forward part 2 through the opening 5 or can be situated in the rear part 3. The injection device 1 is operated as follows. The forward edge 15 of the needle cover 12 is placed on the tissue. The semi-circular forward edge 15 and the side walls 37 ensure that the injection device 1 is placed substantially perpendicular to the tissue and that the injection needle is injected substantially perpendicular into the tissue. This takes place in the forward protective position of the needle cover 12 as shown in FIG. 2. In this position, latching means (not shown) secure the forward element 14 of the needle cover 12, such that it cannot be retracted into the rear element 13. Once the latching means are unlatched, the forward element 14 can be retracted until a rear extreme position is reached. The rear extreme position can be set by a stopper (not shown) that can be provided in the casing of the injection device 1 or in the needle cover 12. By pressing an activating button 9 (or other switch) the fluid product is injected into the tissue mechanically or power-assisted, wherein a piston provided in the ampoule 10 pushes fluid product through an injection needle (not shown) into the tissue. The dose administered can be predetermined by the dosing wheel 6 or by an electronic control system.

Once the fluid product has been administered, the injection needle is extracted by withdrawing the injection device 1 from the tissue. Due to the restoring force of the spring 28, this also retracts the forward element 14 of the needle cover 12 until the forward protective position is reached again. Once the latching means are latched, the position of the forward element 14 is again kept from moving so that the forward element 14 cannot be inadvertently or unintentionally retracted.

In order to replace the ampoule 10, the forward element 14 can be retracted beyond the rear extreme position predetermined by the stopper, so that the forward edge of the ampoule 10 can be handled.

In order to secure the forward protective position of the forward element 14, latching means (not shown) are provided which in a first latching position prevent the forward element 14 from being retracted into the rear element 13. When the latching means are in a released position they allow the forward element 14 to be retracted. Locking sliders, mechanical switches, or anti-twist devices may optionally be integrated into the guiding groove 16 or electromagnetic switches and the like can be provided.

Figure 8:
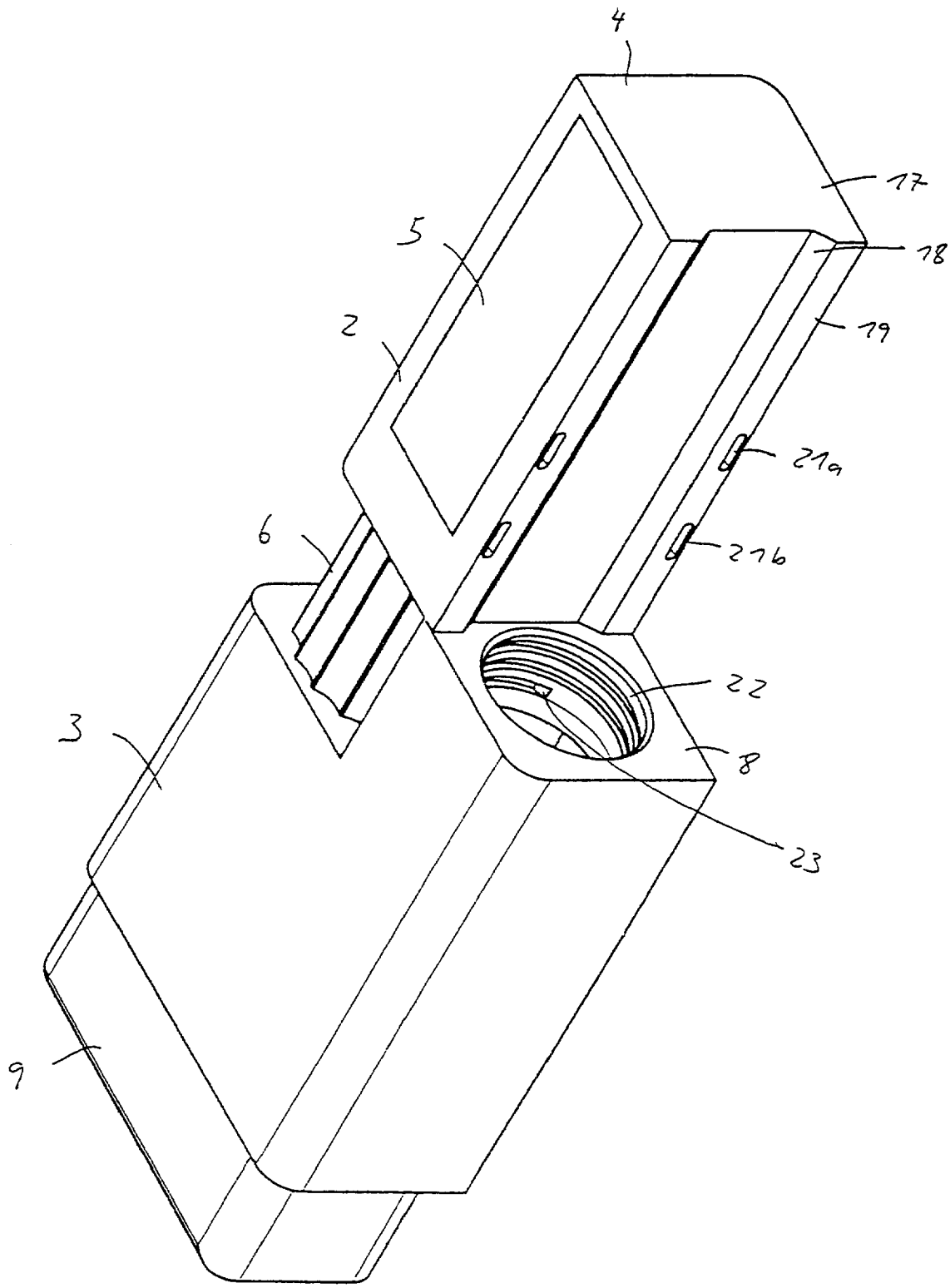
FIG. 8 illustrates the injection device of FIG. 6, without the needle cover.
Figure 9:
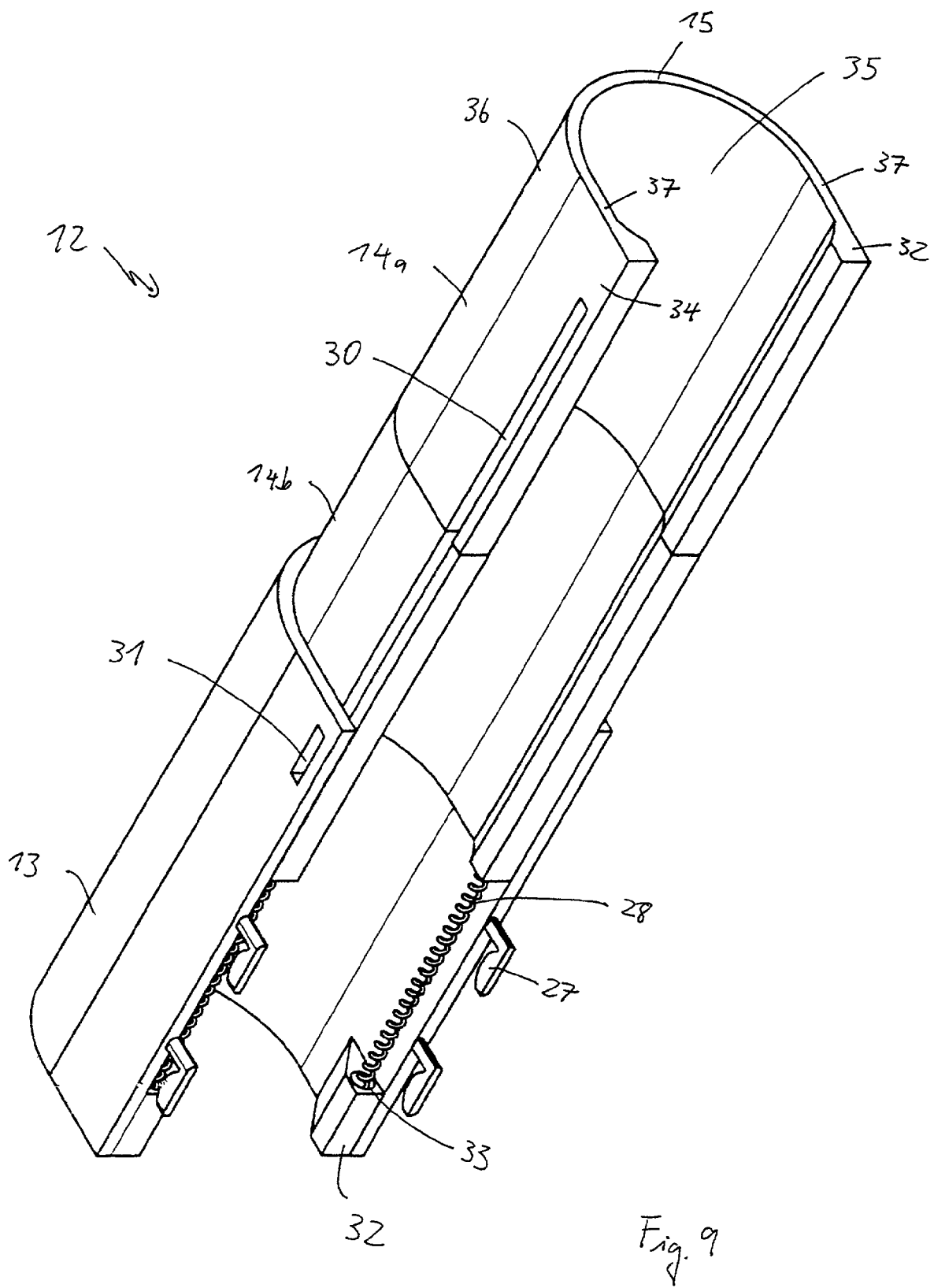
FIG. 9 is a perspective view of a needle cover in accordance with a second embodiment of the present invention.

FIGS. 6 to 11 illustrate another embodiment of a needle covering device. FIG. 9 illustrates the forward element 14 and the rear element 13. The guiding groove 30 does not extend along the entire length of the forward element 14. Rather, a guiding stopper 34 is provided near the forward edge 15 where the guiding groove 30 terminates. The guiding stopper 34 establishes the extreme forward position of the forward element 14. The guiding protrusion 31 interconnects with the guiding groove 30. The guiding protrusion 15 formed as a relatively short projection and is situated near the forward edge of the rear element 13.

The rear element 13 includes two extended sections 32 on a lower edge. The extended sections abut the extended sections 32 of the forward element 14 to establish the rear extreme position of the forward element 14.

Figure 10:
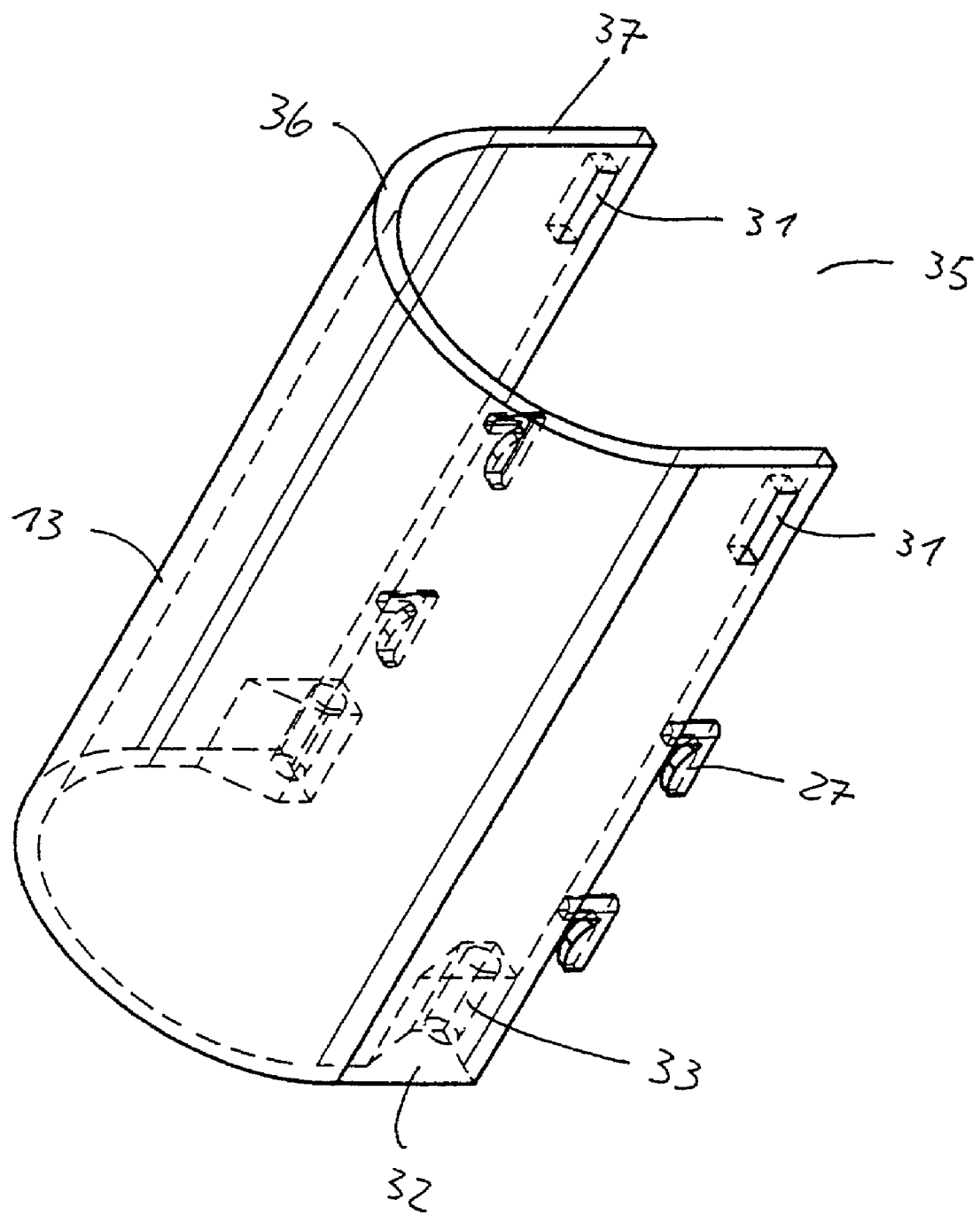
FIG. 10 illustrates the rear element of the needle cover of FIG. 9.
Figure 11:
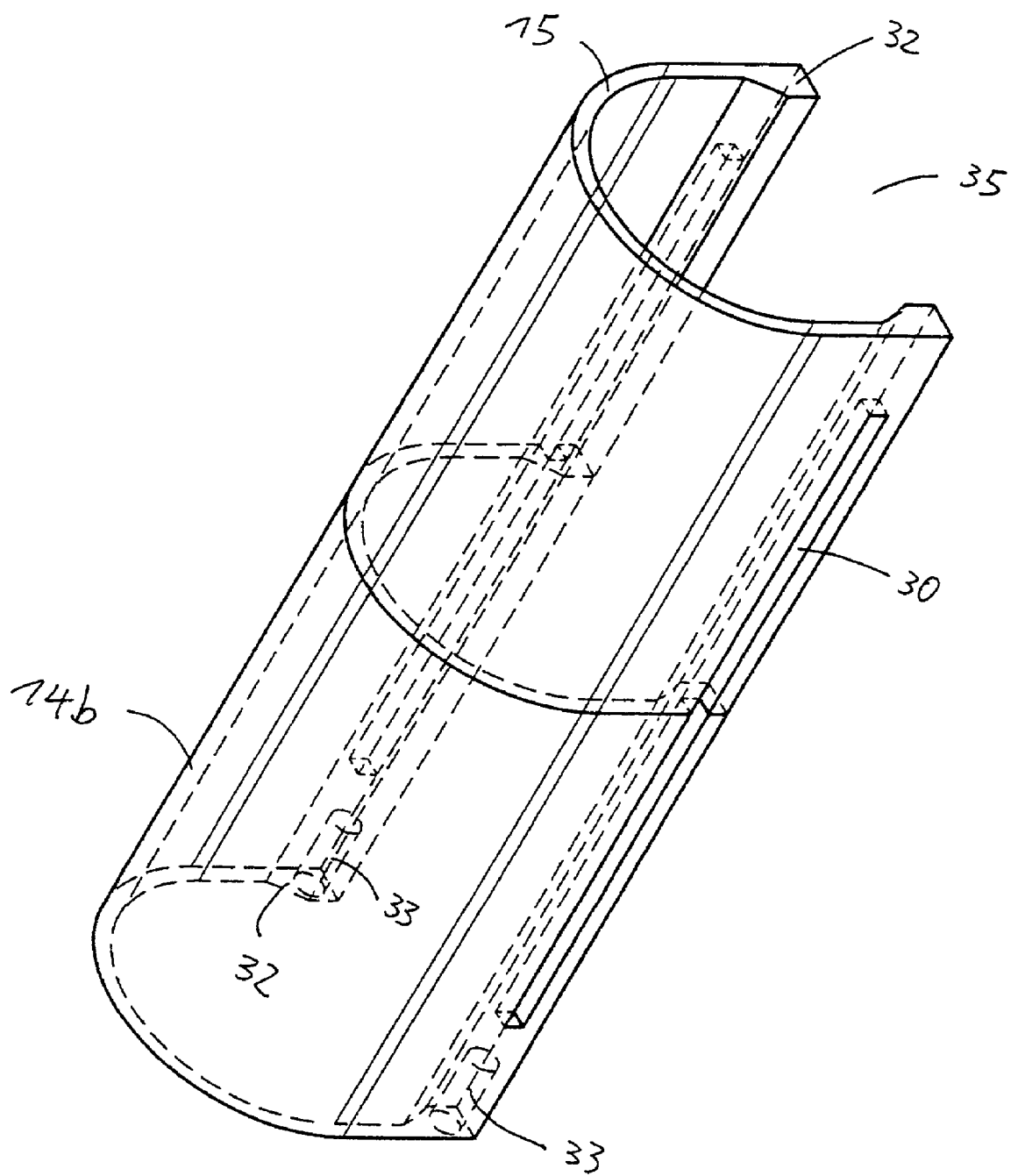
FIG. 11 illustrates the forward element of the needle cover of FIG. 9.

As shown in FIGS. 10 and 11, recesses 33 are provided in the extended sections 32 of each of the rear element 13 and the forward element 14. The recesses serve to accommodate the spring 28 shown in FIG. 9, which serves as the restoring element. A longitudinal guide can be provided to stabilize the restoring element. The longitudinal guide can be a sleeve which can be slid onto the restoring element 28. In order to join the needle cover 12 together, the guiding protrusion 31 is inserted into the guiding groove 30, then the forward element is moved to the forward extreme position and then the spring 28 is inserted into the recesses 33.

The needle cover 12 is placed on the inner side 17 of the forward part 2, as shown in FIG. 8. The attaching or locking elements 27 interconnect with the recesses 21a, 21b provided on the lateral edge 19 of the inner side. Longitudinal slits do not need to be provided on the inner side 17 of the forward part 2. The restoring springs 28 are not arranged in the forward part 2 of the injection device, but rather integrated into the needle covering device 12. The mountings for the restoring springs 28 are arranged outside the center of the needle cover 12.

Although the invention has been described above in connection with injection devices which inject the fluid product from an elongated ampoule, the present invention is not limited to such injection devices. Rather, the principle of laterally arranging a needle cover on an injection device wherein the needle cover can be applied to any shapes of fluid product reservoirs and any designs of injection devices. In some embodiments, the needles can be 30-guage or 31-guage needles.

While the movable casing and/or the needle cover immediately surrounds the reservoir and/or injection needle in some embodiments, a casing jacket may jointly encase the reservoir and the injection needle, and the non-movable casing portions in other embodiments. This casing jacket maybe movable in the manner of the needle cover described above, that is in the axial direction of the reservoir and/or the injection device.

Although the present invention has been described with reference to preferred embodiments, persons skilled in the art will recognize that changes may be made in form and detail without departing from the spirit and scope of the invention.

We claim:

1. An injection device for injecting a fluid product from a reservoir in an injection direction, comprising:
   a) a casing having at least a first retractable casing portion and a second fixed casing portion;
   b) a mounting for receiving said reservoir, wherein the second fixed casing portion is fixedly attached to the mounting and extends a first, fixed length along an axial direction of the reservoir, wherein the first fixed length is less than a total length of the reservoir in the axial direction, and the first retractable casing portion is slidably attached to the second fixed casing portion, wherein the reservoir is not accessible for replacement when the first retractable casing portion is extended in the injection direction and the reservoir becomes accessible when the first retractable casing portion is retracted in a direction opposite to the injection direction by telescoping the first retractable casing portion into the second fixed casing portion; and
   c) an activating element for triggering fluid product administering.

2. The injection device of claim 1, wherein said first retractable casing portion can be retracted in the direction opposite the injection direction beyond a forward end of said reservoir.

3. The injection device as set forth in claim 1, wherein said reservoir is laterally attached to said casing.

4. The injection device as set forth in claim 1, wherein said first retractable casing portion serves as a needle cover.

5. The injection device as set forth in claim 4, wherein said needle cover is tube-shaped and, as seen in cross-section has a semi-circular section and two side wall sections running substantially in a straight line.

6. The injection device as set forth in claim 4, wherein said needle cover comprises at least one guiding element for longitudinally guiding the said needle cover on said casing of said injection device.

7. The injection device as set forth in claim 6, wherein said guiding element is a protrusion for interconnection with a longitudinal slit of said injection device.

8. The injection device as set forth in claim 7, wherein a restoring element for restoring said needle cover to a forward protective position is supported on said protrusion.

9. The injection device as set forth in claim 4, wherein said needle cover comprises at least one attaching element for laterally attaching said needle cover to said casing of said injection device.

10. The injection device as set forth in claim 4, further including a latching means to prevent said cover from retracting in said forward protective position and from said retracted position, in a latching position of said latching means.

11. The injection device as set forth in claim 4, wherein at least one mounting for a restoring element is arranged outside the center of said device.

12. The injection device as set forth in claim 4, wherein said needle cover includes a transparent portion and an opaque portion that obscures said injection needle.

13. The injection device as set forth in claim 4, wherein at least one longitudinal slit is provided in said casing of said injection device, and at least one protrusion of said needle covering meshes with said at least one longitudinal slit, respectively.

14. The injection device as set forth in claim 4, further including a latching means to prevent said needle cover from retracting in said forward protective position and/or in said retracted position, in a latching position of said latching means.

15. The injection device as set forth in claim 4, wherein said needle cover includes a rear and a forward element which are longitudinally movable relative to each other, wherein said rear element includes a guiding element corresponding to a guiding element of said forward element and co-operating with it, to enable said forward element to be guided when it is retracted.

16. The injection device as set forth in claim 15, wherein said rear element includes at least one attaching element, to immovably attach said rear element to said injection device.

17. The injection device as set forth in claim 15, wherein said rear and said forward element each comprise an extended section comprising a mounting for holding a restoring element.

18. The injection device as set forth in claim 1, further including an electronic system for setting a quantity of said fluid product to be administered and for controlling the administering of said fluid product during an injection.

19. The injection device as set forth in claim 1, further including a casing jacket which surrounds said first retractable casing portion and at least partially surrounds at least one of said second fixed casing portion and casing.

20. An injection device comprising:
   a housing;
   a reservoir to which an injection needle can be coupled to deliver a fluid product;
   a fixed rear casing coupled to the housing and extending a first, fixed length along an axial direction the reservoir, wherein the first fixed length is less than a total length of the reservoir in the axial direction;
   a retractable forward casing moveably coupled to the rear casing, wherein the reservoir is not accessible for replacement when the retractable forward casing is extended in an injection direction and the reservoir becomes accessible when the retractable forward casing is retracted in a direction opposite to the injection direction by telescoping the retractable forward casing into the fixed rear casing and wherein the forward casing and the rear casing maintain a coaxial relationship when in the extended position and the retracted position.

21. The injection device of claim 20 wherein the forward casing is biased towards the extended position.

22. The injection device of claim 21 wherein the forward casing is biased by a spring.

23. The injection device of claim 20 wherein the forward casing has an opaque portion to prevent viewing of an injection needle through a sidewall of the forward casing when in an extended position.

24. The injection device of claim 23 wherein the forward casing includes a transparent portion that allows viewing of the reservoir when in the extended position.

25. An injection device for injecting a fluid product from a reservoir, comprising:
   a) a casing having at least a first retractable casing portion and a second fixed casing portion;
   b) a mounting for receiving said reservoir, wherein the second fixed casing portion is fixedly attached to the mounting and extends a first, fixed length along an axial direction the reservoir, wherein the first fixed length is less than a total length of the reservoir in the axial direction, and the first retractable casing portion is slidably attached to the second fixed casing portion;
   c) an activating element for triggering fluid product administering, wherein the reservoir is not accessible for replacement when the first retractable casing portion is extended in the injection direction and the reservoir becomes accessible when the first retractable casing portion is retracted in a direction opposite to the injection direction by telescoping the first retractable casing portion into the second fixed casing portion, and wherein the first retractable casing portion simultaneously serves as a needle cover comprising at least one guiding element, the guiding element being a protrusion for interconnection with a longitudinal slit of said injection device for longitudinally guiding the cover on the casing of said injection device; and
   d) a restoring element supported on said protrusion for restoring said cover to a forward protective position.

* * * * *